(12) United States Patent
Hsieh et al.

(10) Patent No.: US 6,493,646 B1
(45) Date of Patent: Dec. 10, 2002

(54) HIGH ORDER PRIMARY DECAY CORRECTION FOR CT IMAGING SYSTEM DETECTORS

(75) Inventors: Jiang Hsieh, Brookfield, WI (US); O. Erdogan Gurmen, Shorewood, WI (US)

(73) Assignee: GE Medical Systems Global Technology Company, LLC, Waukesha, WI (US)

( * ) Notice: Subject to any disclaimer, the term of this patent is extended or adjusted under 35 U.S.C. 154(b) by 0 days.

(21) Appl. No.: 09/505,590

(22) Filed: Feb. 16, 2000

(51) Int. Cl.[7] .............................................. G06F 19/00
(52) U.S. Cl. .......................... 702/104; 378/19; 375/230
(58) Field of Search .......................... 702/104; 378/19; 375/230

(56) References Cited

U.S. PATENT DOCUMENTS 3,573,624 A * 4/1971 Hartmann ..................... 325/42
5,249,123 A 9/1993 Hsieh ........................... 378/19
5,265,013 A 11/1993 King et al. .................... 378/19
5,331,682 A * 7/1994 Hsieh ........................... 378/19

* cited by examiner

Primary Examiner—John S. Hilten
Assistant Examiner—Stephen J. Cherry
(74) Attorney, Agent, or Firm—Carl B. Horton, Esq.; Armstrong Teasdale LLP

(57) ABSTRACT

Degradation in reconstructed medical images is reduced by a method for calibrating a primary decay correction for a radiation detector having a decay curve that can be characterized by a plurality of components having different time constants. The method includes steps of: fitting the decay curve to a sum of a plurality of weighted exponentials having a first set of time constants; applying a correction to a measured response of the detector using a sum of the plurality of weighted exponentials having the first set of time constants to obtain a corrected response; selecting at least one additional exponential time constant dependent upon the corrected response; and fitting the decay curve to a sum of a second plurality of weighted exponentials including the first plurality of time constants and the at least one additional exponential time constant.

17 Claims, 3 Drawing Sheets

HIGH ORDER PRIMARY DECAY CORRECTION FOR CT IMAGING SYSTEM DETECTORS

BACKGROUND OF THE INVENTION

This application relates to methods for correction of high-order primary decay in detectors, and more particularly to methods providing increased flexibility in defining shapes of corrected decay curves in detectors.

As used herein, the term "primary decay" refers to the fastest exponential decay component of a scintillator. "Afterglow" refers to remaining, slower decay components.

In at least one known computed tomography (CT) imaging system configuration, an x-ray source projects a fan-shaped beam which is collimated to lie within an X-Y plane of a Cartesian coordinate system and generally referred to as the "imaging plane". The x-ray beam passes through the object being imaged, such as a patient. The beam, after being attenuated by the object, impinges upon an array of radiation detectors. The intensity of the attenuated beam radiation received at the detector array is dependent upon the attenuation of the x-ray beam by the object. Each detector element of the array produces a separate electrical signal that is a measurement of the beam attenuation at the detector location. The attenuation measurements from all the detectors are acquired separately to produce a transmission profile.

In known third generation CT systems, the x-ray source and the detector array are rotated with a gantry within the imaging plane and around the object to be imaged so that the angle at which the x-ray beam intersects the object constantly changes. A group of x-ray attenuation measurements, i.e., projection data, from the detector array at one gantry angle is referred to as a "view". A "scan" of the object comprises a set of views made at different gantry angles, or view angles, during one revolution of the x-ray source and detector. In an axial scan, the projection data is processed to construct an image that corresponds to a two dimensional slice taken through the object. One method for reconstructing an image from a set of projection data is referred to in the art as the filtered back projection technique. This process converts the attenuation measurements from a scan into integers called "CT numbers" or "Hounsfield units", which are used to control the brightness of a corresponding pixel on a cathode ray tube display.

It is known to use europium-containing polycrystalline ceramic scintillators in detector arrays of computed tomographic (CT) imaging systems. Such scintillators exhibit much lower hysteresis and radiation damage than other known solid state detectors, such as $CdWO_4$. In addition, the detector material is highly transparent, resulting in higher light output. Detection quantum efficiency (DQE) of 98% or more at 3 mm depth is obtained in a clinical x-ray energy range, resulting in improved image quality. Nevertheless, output signal decay, as indicated by its primary decay, is relatively slow (close to 1 millisecond), discouraging use of these otherwise advantageous scintillators at fast sampling rates at high scanning speeds. An exemplary decay curve is shown in FIG. 3.

It has been shown that a slow primary speed of the detector degrades spatial resolution of a CT imaging system, especially at higher scanning speeds. For example, a scan at 0.5 seconds per rotation will be degraded relative to a scan at 1.0 seconds per rotation, resulting from the significantly increased sampling rate. To overcome this shortcoming, recursive correction algorithms have been proposed.

Corrections using recursive correction algorithms compensate not only for the effects of the primary speed component of the detector response, but also for the afterglow components. Known techniques perform satisfactorily for scan speeds up to 1.0 second using scintillation materials having a decay characteristic such as that illustrated in FIG. 3. For faster scan speeds. however, undershoot and overshoot on the decay curve will occur, resulting in streak artifacts in reconstructed images. This undershoot and overshoot phenomenon is not an intrinsic feature of the decay of this scintillation material, but rather is a side effect of the signal restoration technique.

It would therefore be advantageous to provide methods to reduce or void undershoot and overshoot of the decay curve and the resulting artifacts in the reconstructed images.

BRIEF SUMMARY OF THE INVENTION

There is therefore provided, in one embodiment, a method for calibrating a primary decay correction for a radiation detector having a decay curve that can be characterized by a plurality of components having different time constants. The method includes steps of fitting the decay curve to a sum of a plurality of weighted exponentials having a first set of time constants; applying a correction to a measured response of the detector using a sum of the plurality of weighted exponentials having the first set of time constants to obtain a corrected response; selecting at least one additional exponential time constant dependent upon the corrected response; and fitting the decay curve to a sum of a second plurality of weighted exponentials including the first plurality of time constants and the at least one additional exponential time constant.

The above described embodiment reduces or avoids undershoot and overshoot of the decay curve and the resulting artifacts in reconstructed images.

DETAILED DESCRIPTION OF THE INVENTION

Figure 1:
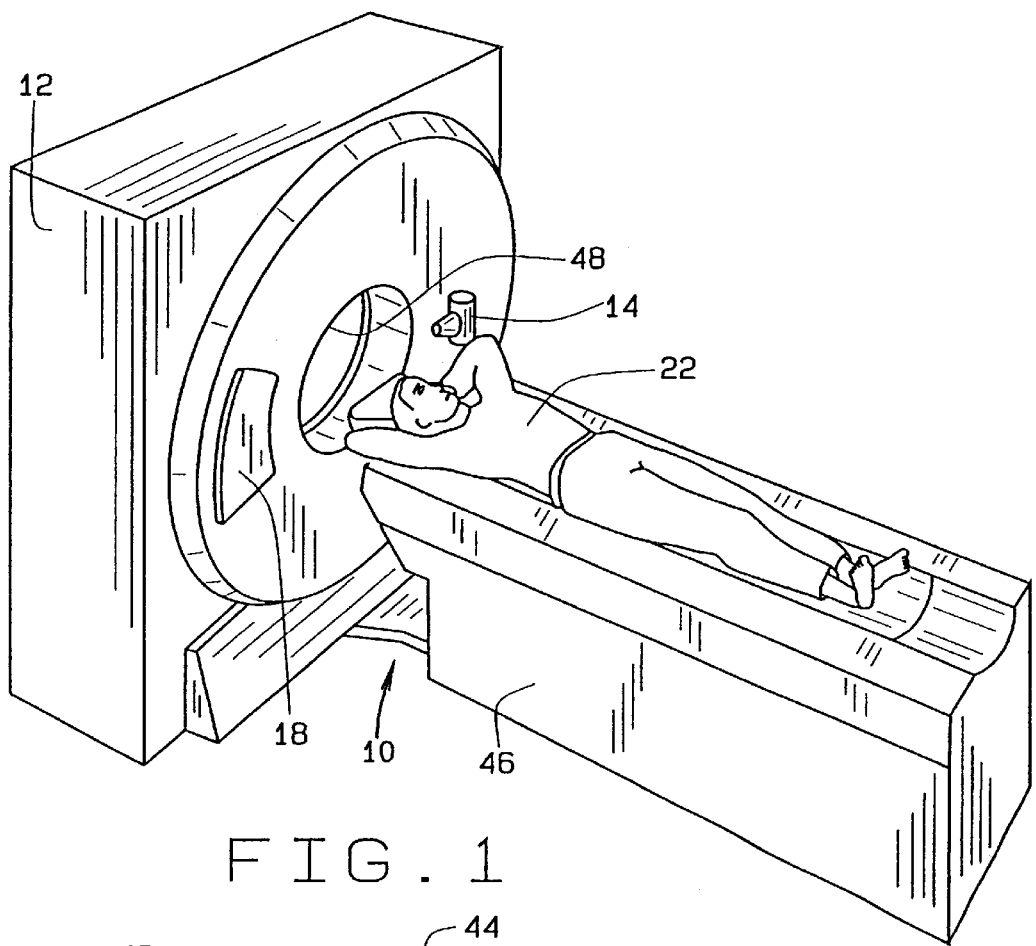
FIG. 1 is a pictorial view of a CT imaging system.
Figure 2:
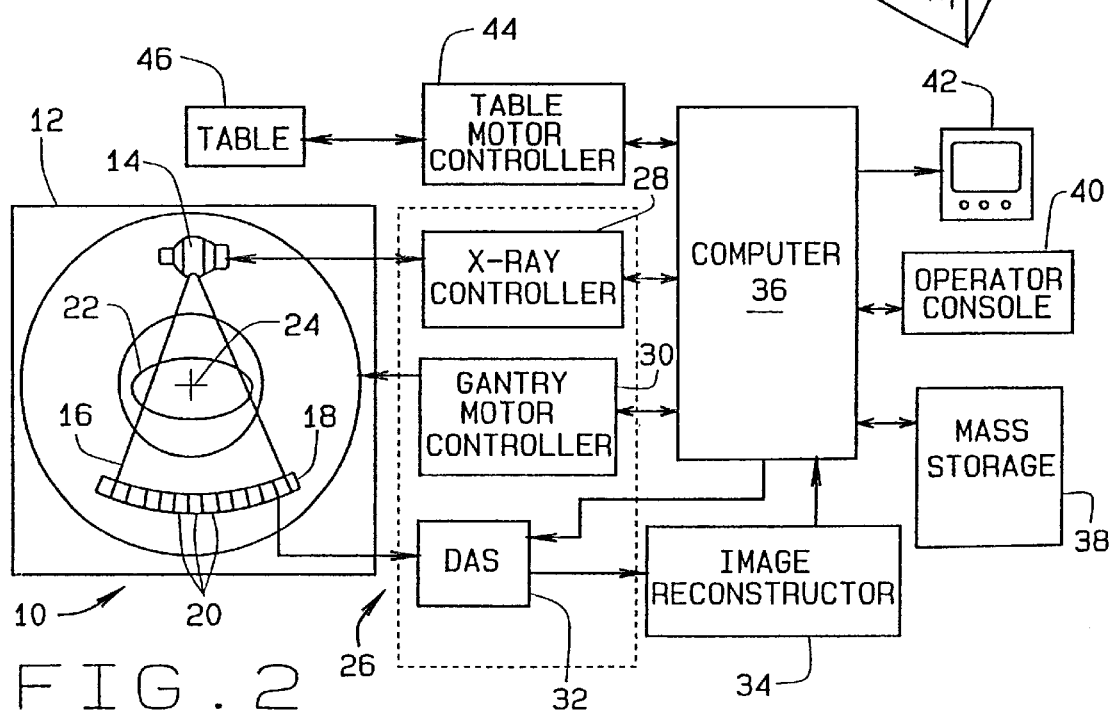
FIG. 2 is a block schematic diagram of the system illustrated in FIG. 1.

Referring to FIGS. 1 and 2, a computed tomography (CT) imaging system 10 is shown as including a gantry 12 representative of a "third generation" CT scanner. Gantry 12 has an x-ray source 14 that projects a beam of x-rays 16 toward a detector array 18 on the opposite side of gantry 12. Detector array 18 is formed by detector elements 20 which together sense the projected x-rays that pass through an object 22, for example a medical patient. Detector array 18 may be fabricated in a single slice or multi-slice configuration. Each detector element 20 produces an electrical signal that represents the intensity of an impinging x-ray beam and hence the attenuation of the beam as it passes through patient 22. During a scan to acquire x-ray projection data, gantry 12 and the components mounted thereon rotate about a center of rotation 24.

Rotation of gantry 12 and the operation of x-ray source 14 are governed by a control mechanism 26 of CT system 10. Control mechanism 26 includes an x-ray controller 28 that provides power and timing signals to x-ray source 14 and a gantry motor controller 30 that controls the rotational speed and position of gantry 12. A data acquisition system (DAS) 32 in control mechanism 26 samples analog data from detector elements 20 and converts the data to digital signals for subsequent processing. An image reconstructor 34 receives sampled and digitized x-ray data from DAS 32 and performs high speed image reconstruction. The reconstructed image is applied as an input to a computer 36 which stores the image in a mass storage device 38.

Computer 36 also receives commands and scanning parameters from an operator via console 40 that has a keyboard. An associated cathode ray tube display 42 allows the operator to observe the reconstructed image and other data from computer 36. The operator supplied commands and parameters are used by computer 36 to provide control signals and information to DAS 32, x-ray controller 28 and gantry motor controller 30. In addition, computer 36 operates a table motor controller 44 which controls a motorized table 46 to position patient 22 in gantry 12. Particularly, table 46 moves portions of patient 22 through gantry opening 48.

Figure 3:
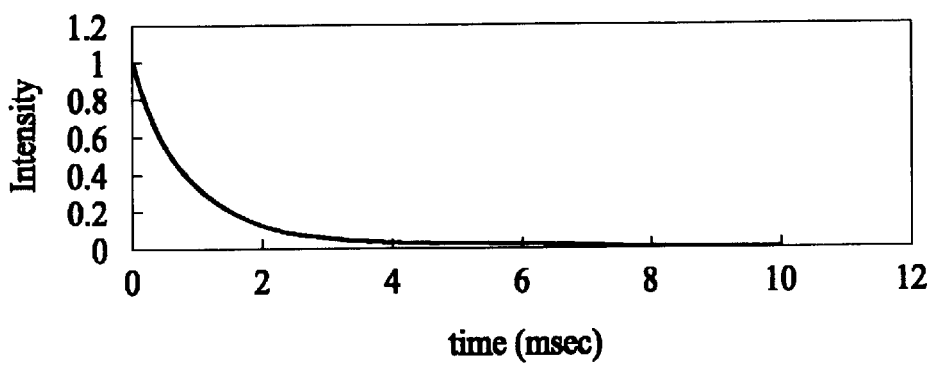
FIG. 3 is a graph of intensity vs. time as measured for an exemplary detector.

In one embodiment of the present invention, detector array 18 comprises detector elements 20 having an empirically determined decay characteristic such as the exemplary decay curve shown in FIG. 3. To obtain a primary speed correction, the primary speed is modeled by multiple exponentials, and decay parameters are determined based on a corrected, minimum least square error (MLSE) fitting of the decay curve to a set of exponential functions.

A primary speed is modeled by multiple exponentials. Decay parameters are determined by an MLSE (minimum least square error) fitting an observed decay curve to a set of exponential functions. A detector impulse response is modeled by an equation written as:

$$h(t) = \sum_{n=1}^{N} \frac{\alpha_n}{\tau_n} e^{-\frac{t}{\tau_n}}, \tag{1}$$

where n designates one of N components of the exponential response which has a relative strength $\alpha_n$ of a decay component having time constant $\tau_n$. The response of one type of detector element 20 has been characterized accurately by four (N=4) such time constant components. Different types of detector elements 20 may require a greater or lesser number of decay components for modeling purposes. The terms "detector element response" and "detector response" are used interchangeably herein. However, detector elements 20 need not have essentially identical responses. Therefore, in at least one embodiment, each detector element response is individually determined and corrected. However, in at least one embodiment, detector elements 20 of detector 18 are all of the same type and have essentially identical responses.

A detector response y(t) to an input signal x(t) is written as a convolution y(t)=h(t)*x(t) of detector impulse response h(t) and input signal x(t):

$$y(t) = \int_{-\infty}^{t} x(t') \sum_{n=1}^{N} \frac{\alpha_n}{\tau_n} e^{-(t-t')/\tau_n} dt' \tag{2}$$

Equation (2) can be simplified because input signal x(t) is a causal function, allowing summation and integration to be interchanged in equation (2). Furthermore, integration region [0,t] can be divided into k intervals corresponding to the period between views with each interval being denoted by $\Delta t$ ($k\Delta t = t$). When these factors are considered, an actual attenuation value $x_k$ for a kth view for relatively small values of $\Delta t$ is written:

$$x_k = \frac{y(k\Delta t) - \sum_{n=1}^{N} \alpha_n (1 - e^{-\Delta t/\tau_n}) \sum_{j=1}^{k-1} x_j e^{-(k-1)\Delta t/\tau_n}}{\sum_{n=1}^{N} \alpha_n (1 - e^{-\Delta t/\tau_n})} \tag{3}$$

where y(k$\Delta$t) is a raw attenuation value from detector element 20 acquired during a kth view. Equation (3) is rewritten in a form:

$$x_k = \frac{y(k\Delta t) - \sum_{n=1}^{N} \beta_n e^{-\Delta t/\tau_n} [x_{k-1} + e^{-\Delta t/\tau_n} [x_{k-2} + \ldots + e^{-\Delta t/\tau_n}(x_2 + e^{-\Delta t/\tau_n} x_1)\ldots]]}{\sum_{n=1}^{N} \beta_n} \tag{4}$$

where $\beta_n = \alpha_n(1 - e^{-\Delta t/\tau_n})$. Denoting the contents enclosed by the outermost brackets in (4) as $S_{nk}$, a recursive relationship is written as:

$$x_k = \frac{y(k\Delta t) - \sum_{n=1}^{N} \left(\beta_n e^{-\frac{\Delta t}{\tau_n}}\right) S_{nk}}{\sum_{n=1}^{N} \beta_n}, \tag{5}$$

where the denominator and bracketed portion of the numerator are constants. The term $S_{nk}$ for the present attenuation value is a function of the term $S_{n(k-1)}$ for the attenuation value from the previous view, the function being written as $S_{nk} = x_{k-1} + e^{\Delta t/\tau_n} S_{n(k-1)}$, where $x_{k-1}$ is the actual attenuation value derived from the detector element 20 signal sample from the previous view. The value of $S_{nk}$ for the first sample is zero. For some CT systems 10, an x-ray signal is turned on briefly before data collection starts. In this case, $S_{nk}$ for the first view is estimated by applying the above recursive relationship for the first view m times to simulate the brief x-ray on condition, where mΔt≈x-ray on time before view 1. Thus, to derive an actual attenuation value from a given detector element 20 signal sample, that sample and data from the processing of an immediately preceding sample must be known. As a result, equation (5) is implemented, in one embodiment, by an array processor as a recursive filter.

To apply the filter function of equation (5) to real image data, a response for each detector element 20 in detector 18 must be characterized by deriving values for $\alpha_n$ and $\tau_n$ for the time constant components of each detector element 20. This derivation is accomplished in a factory by a process that includes operating CT system 10 without an object present to image. An x-ray source 14 of CT imaging system 10 is turned on at a time $t_0$. In one embodiment, x-ray source 14 is turned on for a period of time long enough to saturate all decay components of the detector, for example, about half the normal scan time. X-ray source 14 is then turned off at a later time $t_1$.

An output signal from each detector element 20 is sampled individually while x-ray beam 16 is active and for a sufficiently long period after the termination of x-ray beam 16 to provide a desired degree of accuracy in characterization. Samples of the detector element 20 signals are stored in an array similar to that used for storing attenuation values while imaging. The detector element 20 response during the characterization process is defined by expressions written as:

$$y(t) = \psi \text{ for } t_0 < t < t_1, \text{ and } y(t) = \psi \sum_{n=1}^{N} \alpha_n e^{(t-t_1)/\tau_n} \text{ for } t \geq t_1 \qquad (6)$$

Samples of detector element 20 output signal that were acquired while x-ray beam 16 is on ($t_0 < t_1 - \delta t < t$), where δt is determined such that the standard deviations of the averaged signal is sufficiently low to provide a desired degree of accuracy in characterization) are averaged and the result is used to derive a value for the x-ray flux intensity Ψ as written in equation (6). The samples acquired after termination of x-ray beam 16 are divided by the value of Ψ to normalize the data, which results in a decay curve similar to that shown in FIG. 3. The logarithm of the normalized data is then taken.

Values for $\alpha_n$ and $\tau_n$ of each time constant component of the exponential response are determined next. The impulse response for one type of CT detector element 20 is characterized by four time constants $\tau_n$ of 1, 6, 40, and about 300 milliseconds, although the exact time constants may vary for other detectors. The time constants $\tau_n$ and their relative strengths $\alpha_n$ are determined, for example, by performing minimum least square error (MLSE) fit of equation (1). To reduce error due to noise, multiple measurements are averaged prior to the fitting.

In another embodiment, $\alpha_n$ and $\tau_n$ are determined one at a time in descending order of $\tau_n$, i.e., longest $\tau_n$ first. A detector sample signal is selected that was acquired at time T (e.g., 300 milliseconds) after the x-ray beam extinguished at which time the effects of all except the longest time constant component are negligible. Using the logarithmic values of the detector samples, equation (6) is simplified to log[y(T)]=log $\alpha_n - (T/\tau_n)$. The simplified equation is solved for $\alpha_4$ of the fourth (n=4) time constant component.

Based on estimated values for $\alpha_4$ and $\tau_4$, the contribution of the longest time constant component to the measured decaying signal data is calculated and removed from that data. The process is repeated for the next longest time constant component $\tau_3$ of the detector response, and so on for each of the remaining components. This characterization process is performed for each of the detector elements 20 in detector 18.

Then the values of $\alpha_n$ and $\tau_n$ are employed to derive the constant terms of equation (5) for each of the four time constant components of the response of every detector element. These constants are stored in tables in the disc memory for later use in filtering real image data. In another embodiment, the constants are calculated just prior to their usage.

Figure 4:
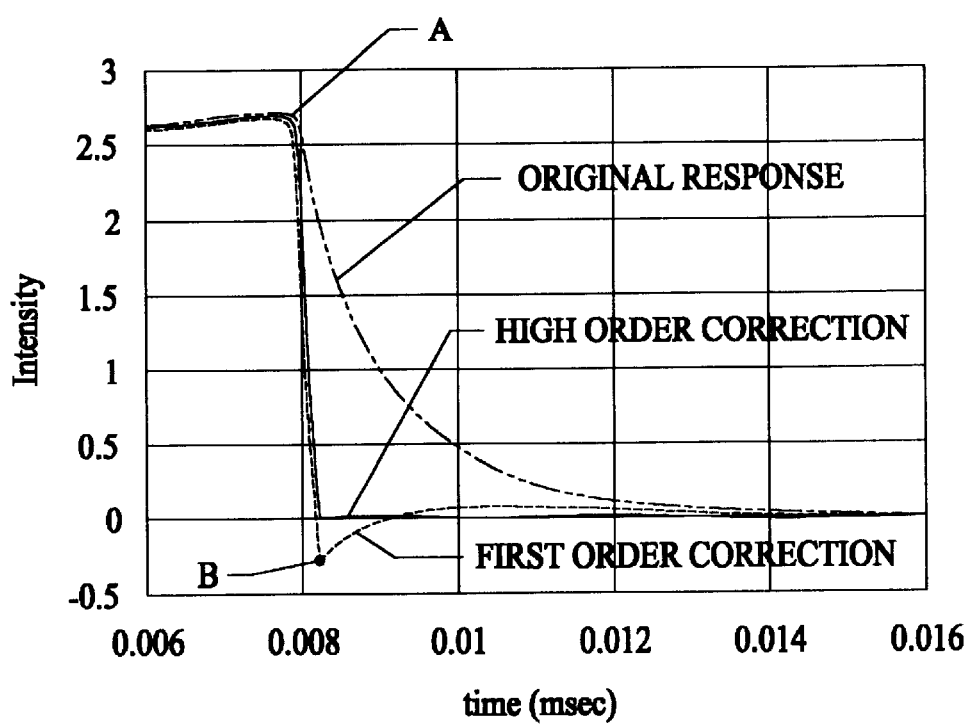
FIG. 4 is a graph of intensity vs. time for an exemplary detector, showing the original response without correction, a first order correction with undershoot and overshoot, and a high order correction correcting the undershoot and overshoot.

After a first MLSE fit is obtained, the correction of equation (5) based on the modeled detector impulse response does not precisely compensate for the measured decay curve of FIG. 3. More specifically, one or more "overshoot" and "undershoot" anomalies will be observed in the modeled detector response. FIG. 4 shows the original response curve of a detector, a corresponding first-order corrected response curve, and a corresponding high-order corrected response curve. The first-order response curve corresponds to the correction after a first MLSE fit is obtained and the correction of equation (5) is applied. Referring to FIG. 4, to provide additional correction for overshoot and/or undershoot anomalies in the first-order corrected response curve, one or more additional, "artificial" time constants τ less than the shortest time constant of the original set of time constants are added. These additional time constants correspond to overshoot and undershoot locations in the corrected detector response. For example, in FIG. 4, an additional time constant τ less than or equal to the difference in time between points A and B of the first-order corrected response curve is selected, in view of the undershoot at B. The one or more additional time constant components τ and corresponding strengths α provide added flexibility in-defining a shape of a corrected decay curve. After the first correction is obtained, a second, better correction is obtained using both the original time constants and the new, additional time constants corresponding to the overshoots and undershoots. For example, all values $\alpha_n$ are determined a second time, using the new, expanded set of time constants $\tau_n$, starting with the longest time constant. In one embodiment, a constraint on both the first and the second, better fit is that the α's sum to unity so that $$\sum_{n=1}^{N} \alpha_n = 1.$$

Once the second, better fitting model is established, recursive primary speed correction is performed using the components τ and α of the second model rather than the first. The better fitting model corresponds to the higher-order corrected response shown in FIG. 4.

It should be apparent that the number of time constants N is greater in the second fitting. Therefore, in one embodiment, subscripts n of time constants $\tau_n$ of the first fitting are renumbered so that these time constants, in combination with the new, "artificial" time constants, maintain the convention of time constants increasing with increasing n. However, the present invention is not dependent upon the use of this notational convention, and its use is merely a convenience.

In one embodiment, CT imaging system 10 is operated (at the factory, for example) to determine the time constants and intensities of the improved correction. Fitting and other steps involving computation are performed utilizing computer 36. In another embodiment, a separate computer (not shown) is used for fitting and/or other steps involving computation.

Figure 5:
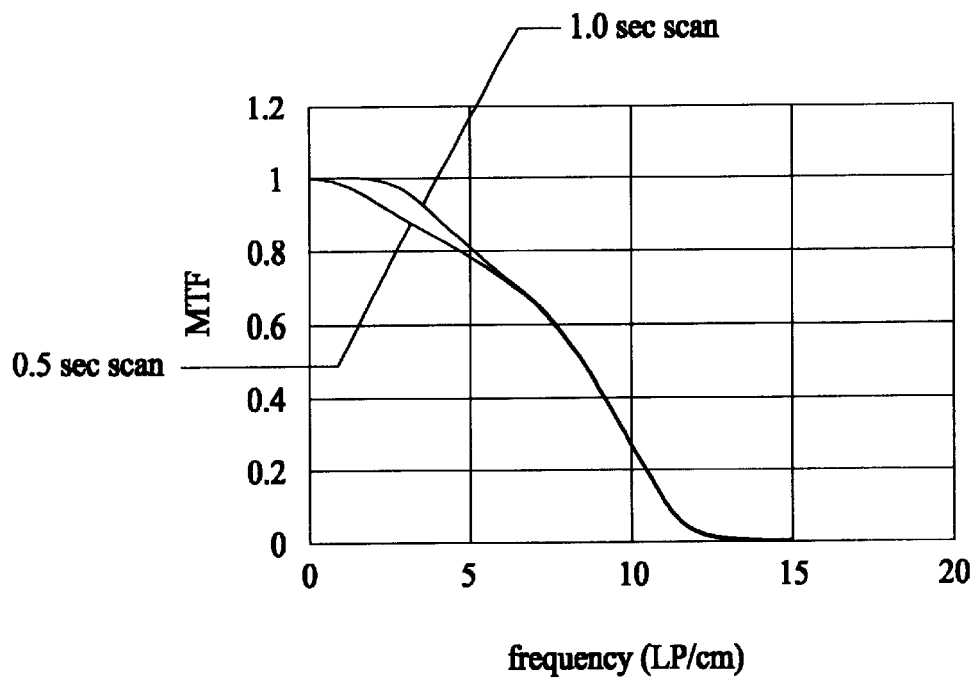
FIG. 5 is a graph of modulation transfer function (MTF) as a function of frequency in line pairs per cm (LP/cm) for two scans of a 0.1 mm thin tungsten wire scanned at 1.0 seconds (solid line) and 0.5 seconds (dashed line) scan speed using an exemplary CT imaging system with a detector having the characteristic graphed in FIG. 3.
Figure 6:
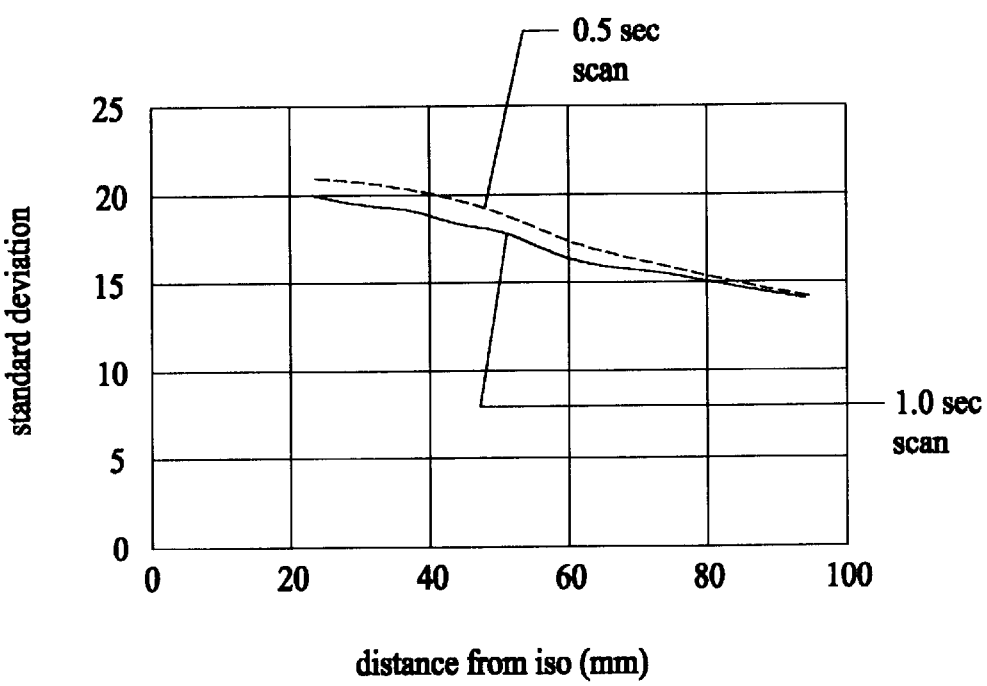
FIG. 6 is a graph of standard deviation as a function of distance from an isocenter for two scans of a 0.1 mm thin tungsten wire scanned at 1.0 seconds (solid line) and 0.5 seconds (dashed line) scan speed using an exemplary CT imaging system with a detector having the characteristic graphed in FIG. 3.

In experiments with phantoms to test the effectiveness of the above embodiments, a 0.1 mm tungsten wire was scanned at both 1.0 second and 0.5 second scan speeds with the same total photon flux. Both modulation transfer function (MTF) and noise were measured. Results are shown in FIGS. 5 and 6. In each figure, the results shown indicate that the faster scan speed (0.5 second) with the correction produce results equivalent to that of the slower scan speed (1.0 second).

From the preceding description of various embodiments of the present invention, it is evident that methods of the present invention are useful in preventing undershoot and overshoot of a modeled detector decay curve. Compensated, reconstructed images using methods of the present invention have correspondingly reduced streak artifacts.

Although particular embodiments of the invention have been described and illustrated in detail, it is to be clearly understood that the same is intended by way of illustration and example only and is not to be taken by way of limitation. In addition, the CT system described herein is a "third generation" system in which both the x-ray source and detector rotate with the gantry. Many other CT systems including "fourth generation" systems wherein the detector is a full-ring stationary detector and only the x-ray source rotates with the gantry, may be used. Moreover, the system described herein performs an axial scan, however, the invention may be also be used with systems employing a helical scan. Accordingly, the spirit and scope of the invention are to be limited only by the terms of the appended claims and legal equivalents.

What is claimed is:

1. A method for calibrating a primary decay correction for a radiation detector is a medical imaging system having a decay curve that can be characterized by a plurality of components having different time constants, said method comprising the steps of:
    fitting the decay curve to a sum of a plurality of weighted exponentials having a first set of time constants;
    applying a correction to a measured response of the detector using a sum of the plurality of weighted exponentials having the first set of time constants to obtain a corrected response;
    determining at least one overshoot of the corrected response;
    determining at least one undershoot of the corrected response;
    determining a time difference between the overshoot and the undershoot;
    selecting at least one additional exponential time constant that is at least one of equal to the time difference and less than the time difference; and
    fitting the decay curve to a sum of a second plurality of weighted exponentials including the first plurality of time constants and the at least one additional exponential time constant.

2. A method in accordance with claim 1 wherein the steps of fitting the decay curve to a sum of a first plurality of weighted exponentials having a first set of time constants and of fitting the decay curve to a sum of a second plurality of weighted exponentials each comprise a minimum least square error (MLSE) fitting.

3. A method in accordance with claim 1 wherein the step of selecting at least one additional exponential time constant comprises the step of selecting at least one additional exponential time constant less than the shortest time constant of the first set.

4. A method in accordance with claim 1 further comprising the step of determining a decay curve of the radiation detector.

5. A method in accordance with claim 4 wherein determining a decay curve of the radiation detector comprises the steps of:
    turning on an x-ray source of the CT system at a time $t_0$ for a period of time long enough to saturate decay components of the radiation detector; and
    turning off the x-ray source at a later time $t_1$.

6. A method in accordance with claim 5 wherein determining a decay curve of the radiation detector further comprises the step of sampling output signals from each detector element of the detector while the x-ray source is on and for a period after the x-ray source is turned off.

7. A method in accordance with claim 6 wherein determining a decay curve of the radiation detector further comprises the steps of averaging samples of detector output signals acquired while the x-ray source is on ($t_0 < t_1 - \delta t < t < t_1$) and deriving a value for x-ray flux intensity $\Psi$ from the averaged samples of detector output signals, wherein detector element response y(t) during the characterization process is written as:

$$y(t) = \psi \text{ for } t_0 < t < t_1, \text{ and } y(t) = \psi \sum_{n=1}^{N} \alpha_n e^{(t-t_1)/\tau_n} \text{ for } t \geq t_1.$$

8. A method in accordance with claim 7 wherein the step of fitting the decay curve to a sum of a first plurality of weighted exponentials having a first set of time constants comprises the step of fitting y(t) for $t > t_1$ to a sum of N selected exponentials having time constants $\tau_n$ and intensities $\alpha_n$.

9. A method in accordance with claim 8 wherein the step of fitting the decay curve to a sum of a first plurality of exponentials comprises determining values of $\alpha_n$ in an order starting with an $\alpha$ corresponding to a longest time constant $\tau$.

10. A method in accordance with claim 9 wherein the step of fitting the decay curve to a sum of a second plurality of weighted exponentials including the first plurality of time constants and the at least one additional exponential time constant comprises the step of fitting y(t) for $t > t_1$ to a sum of N selected exponentials having time constants $\tau_n$ and intensities $\alpha_n$, the value of N being greater than during the step of fitting the decay curve to a sum of the first plurality of weighted exponentials, and further comprising the steps of constraining $$\sum_{n=1}^{N} \alpha_n = 1$$

in each of said fitting steps.

11. A method for operating a medical imaging system having a radiation detector that can be characterized by a plurality of components having different time constants, said method comprising the steps of:
    fitting a decay curve of the radiation detector to a sum of a plurality of weighted exponentials having a first set of time constants;
    applying a correction to a measured response of the detector using a sum of the plurality of weighted exponentials having the first set of time constants to obtain a corrected response;

determining at least one overshoot of the corrected response;

determining at least one undershoot of the corrected response;

determining a time difference between the overshoot and the undershoot;

selecting at least one additional exponential time constant that is at least one of equal to the time difference and less than the time difference;

fitting the decay curve to a sum of a second plurality of weighted exponentials including the first plurality of time constants and the at least one additional exponential time constant, wherein the second plurality of weighted exponentials comprises exponentials having time constants $\tau_n$ and corresponding strengths $\alpha_n$;

exposing an object to a beam of radiation from the medical imaging system;

acquiring a first set of radiation attenuation values by periodically sampling at an interval $\Delta t$ a signal produced by the radiation detector, where $y(k\Delta t)$ designates a value in the first set acquired during a kth sampling interval;

producing a second set of data values from the first set of radiation attenuation values, in which each data value $x_k$ is defined by an equation written as:

$$x_k = \frac{y(k\Delta t) - \sum_{n=1}^{N}\left(\beta_n e^{-\frac{\Delta t}{\tau_n}}\right)S_{nk}}{\sum_{n=1}^{N}\beta_n},$$

where:

$\beta_n = \alpha_n(1-e^{-\Delta t/\tau_n})$;

$S_{nk} = X_{k-1} + e^{-\Delta t/\tau_n}S_{n(k-1)}$ and a value of $S_{nk}$ for the first sample is zero; and reconstructing an image of the object from the second set of data values.

12. A method in accordance with claim 11 wherein the steps of fitting the decay curve to a sum of a first plurality of weighted exponentials having a first set of time constants and of fitting the decay curve to a sum of a second plurality of weighted exponentials each comprise a minimum least square error (MLSE) fitting.

13. A method in accordance with claim 11 wherein the step of selecting at least one additional exponential time constant comprises the step of selecting at least one additional exponential time constant less than a shortest time constant of the first plurality of weighted exponentials.

14. A method in accordance with claim 11 further comprising the step of determining a decay curve of the radiation detector.

15. A method in accordance with claim 14 wherein determining a decay curve of the radiation detector comprises the steps of:

turning on an x-ray source of the CT system at a time $t_0$ for a period of time long enough to saturate decay components of the radiation detector; and turning off the x-ray source at a later time $t_1$.

16. A method in accordance with claim 15 wherein determining a decay curve of the radiation detector further comprises the step of sampling output signals from each detector element of the detector while the x-ray source is on and for a period of time after the x-ray source is turned off.

17. A method in accordance with claim 16 wherein determining a decay curve of the radiation detector further comprises the steps of averaging samples of detector output signals acquired while the x-ray source is on ($t_0 < t_1 - \delta t < t < t_1$) and deriving a value for x-ray flux intensity $\Psi$ from the averaged samples of detector output signals, wherein detector element response $y(t)$ during the characterization process is written as:

$$y(t) = \psi \text{ for } t_0 < t < t_1, \text{ and } y(t) = \psi\sum_{n=1}^{N}\alpha_n e^{(t-t_1)/\tau_n} \text{ for } t \geq t_1.$$

* * * * *